(12) United States Patent
Loprete

(10) Patent No.: US 12,151,212 B2
(45) Date of Patent: Nov. 26, 2024

(54) METHOD FOR HUMIDIFYING FACILITATED-TRANSPORT MEMBRANES

(71) Applicant: COMPACT MEMBRANE SYSTEMS INC., Newport, DE (US)

(72) Inventor: Kenneth Evan Loprete, Cherry Hill, NJ (US)

(73) Assignee: Compact Membrane Systems, Inc., Newport, DE (US)

( * ) Notice: Subject to any disclaimer, the term of this patent is extended or adjusted under 35 U.S.C. 154(b) by 706 days.

(21) Appl. No.: 17/276,639

(22) PCT Filed: Sep. 26, 2019

(86) PCT No.: PCT/US2019/053236
§ 371 (c)(1),
(2) Date: Mar. 16, 2021

(87) PCT Pub. No.: WO2020/091920
PCT Pub. Date: May 7, 2020

(65) Prior Publication Data
US 2021/0268445 A1    Sep. 2, 2021

Related U.S. Application Data

(60) Provisional application No. 62/737,704, filed on Sep. 27, 2018.

(51) Int. Cl.
*B01D 65/00*    (2006.01)
*B01D 53/22*    (2006.01)
(Continued)

(52) U.S. Cl.
CPC ........... *B01D 65/00* (2013.01); *B01D 53/228* (2013.01); *B01D 63/10* (2013.01); *B01D 71/32* (2013.01); *C07C 7/144* (2013.01)

(58) Field of Classification Search
CPC ...... B01D 65/00; B01D 53/228; B01D 63/10; B01D 71/32; B01D 2257/108;
(Continued)

(56) References Cited

U.S. PATENT DOCUMENTS 4,174,374 A * 11/1979 Matson ................ B01D 53/228
423/220
4,239,506 A * 12/1980 Steigelmann ........... C07C 7/152
210/651
(Continued)

FOREIGN PATENT DOCUMENTS

CN    105683222 A    6/2016
EP    2737938 A1    6/2014
(Continued)

OTHER PUBLICATIONS

Office Action from Japanese Patent Application No. 2021-517304.
(Continued)

*Primary Examiner* — Stephen Hobson
(74) *Attorney, Agent, or Firm* — Seed IP Law Group LLP

(57) ABSTRACT

An improved method for humidification of a facilitated-transport membrane incorporates delivering a non-selective hydration fluid incorporating liquid water to a permeate side of a pressure vessel containing the facilitated transport membrane. The non-selective hydration fluid includes water and may be configured on the permeate side interface of the facilitated-transport membrane as a liquid or a gas. A process for separation of components in a gaseous mixture utilizing the method for humidification produces higher permeation of gasses through the facilitated transport membrane. The non-selective hydration fluid may be static or flowing and is non-selective for the permeance of certain permeate-gas components over other components.

14 Claims, 2 Drawing Sheets

(51) Int. Cl.
  *B01D 63/10* (2006.01)
  *B01D 71/32* (2006.01)
  *C07C 7/144* (2006.01)

(58) Field of Classification Search
  CPC ...... B01D 2257/504; B01D 2257/7022; B01D 2257/80; B01D 61/38; B01D 69/142; C07C 7/144; Y02C 20/40
  See application file for complete search history.

(56) References Cited

U.S. PATENT DOCUMENTS

| | | | | |
|---|---|---|---|---|
| 4,318,714 | A * | 3/1982 | Kimura | B01D 53/228 96/4 |
| 4,741,744 | A * | 5/1988 | Wu | B01D 71/32 95/55 |
| 4,750,918 | A * | 6/1988 | Sirkar | B01D 53/229 96/5 |
| 5,057,641 | A * | 10/1991 | Valus | B01D 63/02 585/818 |
| 5,191,151 | A * | 3/1993 | Eriksen | B01D 71/76 585/818 |
| 5,863,610 | A * | 1/1999 | Young | B01J 31/10 427/350 |
| 10,029,248 | B2 * | 7/2018 | Feiring | B01D 71/76 |
| 2002/0144899 | A1 * | 10/2002 | Arcella | B01D 71/32 521/27 |
| 2002/0144944 | A1 * | 10/2002 | Arcella | B01D 67/0093 210/488 |
| 2003/0035898 | A1 * | 2/2003 | Sanguineti | H01M 8/1062 427/385.5 |
| 2012/0118816 | A1 * | 5/2012 | Gjoka | B01D 67/0006 106/287.23 |
| 2014/0137740 | A1 * | 5/2014 | Aburaya | B01D 69/142 427/244 |
| 2015/0025293 | A1 * | 1/2015 | Feiring | B01J 41/14 585/818 |
| 2015/0217232 | A1 * | 8/2015 | MacCallum | B01D 61/364 210/321.64 |
| 2016/0056483 | A1 * | 2/2016 | Scherer | B32B 38/0004 156/60 |
| 2016/0303837 | A1 * | 10/2016 | Chou | B32B 5/022 |
| 2017/0073250 | A1 * | 3/2017 | MacCallum | B01D 61/364 |
| 2018/0093230 | A1 * | 4/2018 | Koizumi | B32B 27/322 |
| 2018/0134638 | A1 * | 5/2018 | Koizumi | C07C 7/005 |
| 2018/0370816 | A1 * | 12/2018 | Bower | B01D 5/006 |
| 2020/0188842 | A1 * | 6/2020 | Loprete | B01D 69/1071 |
| 2020/0238224 | A1 * | 7/2020 | Majumdar | B01D 67/0093 |
| 2024/0024822 | A1 * | 1/2024 | Merrill | B01D 53/228 |
| 2024/0051832 | A1 * | 2/2024 | Gadikota | C01B 32/50 |
| 2024/0200208 | A1 * | 6/2024 | Huo | C25B 15/087 |

FOREIGN PATENT DOCUMENTS

| | | | | |
|---|---|---|---|---|
| JP | 2013-022581 A | | 2/2013 | |
| JP | 2014-079754 A | | 5/2014 | |
| JP | 2016-529095 A | | 9/2016 | |
| WO | WO 2015-009969 A1 | | 1/2015 | |
| WO | WO-2023287628 A1 | * | 1/2023 | ........... B01D 53/228 |
| WO | WO-2024044132 A1 | * | 2/2024 | |

OTHER PUBLICATIONS

Asim K. Guha et al., "Gas separation modes in a hollow fiber contained liquid membrane permeator", Industrial & Engineering Chemistry Research, vol. 31, No. 2, Feb. 1, 1992, pp. 593-604.
Teramoto et al., "Separation of ethylene from ethane by a flowing liquid membrane using silver nitrate as a carrier," Journal of Membrane Science Jul. 1989, vol. 45 (1-2), pp. 115-136.
International Search Report for PCT/US2019/053236.
Written Opinion for PCT/US2019/053236.
Office Action from Chinese Patent Application No. 201980057895.3.
Zook et al., "Density and Solubility of Nafion: Recast, Annealed, and Commercial Films," *Analytical Chemistry* 68(21):3793-3796, Nov. 1, 1996 (4 pages).

* cited by examiner

METHOD FOR HUMIDIFYING FACILITATED-TRANSPORT MEMBRANES

CROSS REFERENCE TO RELATED APPLICATIONS

This application claims the benefit of priority to U.S. Provisional Patent Application No. 62/737,704, filed on Sep. 27, 2018, the entirety of which is hereby incorporated by reference herein.

GOVERNMENT RIGHTS

This invention was made with government support under DE-SC0017086 awarded by the Department of Energy. The government has certain rights in the invention.

FIELD OF THE INVENTION

A method for humidifying a facilitated-transport membrane in which a non-selective hydration fluid comprising liquid water is brought within the permeate side of the vessel containing the facilitated-transport membrane; processes for separating gaseous mixtures with the humidified facilitated-transport membrane are disclosed.

BACKGROUND

Facilitated-transport membranes are a promising technology for commercialization in areas such as alkene separation from alkanes in petrochemical refineries, carbon dioxide ($CO_2$) separation from nitrogen in flue gas, $CO_2$ separation from methane in biogas, and $CO_2$ separation from hydrogen in other industrial processes. With permeability and selectivity that can exceed the Robeson upper bound for most other membrane separations, the use of facilitated-transport membranes could greatly reduce the amount of energy needed for industrial separations. Their use may also enable efficient capture of waste gas emissions, thus reducing the impact on the environment. However, there are several challenges to overcome for wide-scale commercialization of this technology such as simplified operation and improved membrane hydration, in particular.

Mass transfer in facilitated-transport membranes that are non-porous operates through traditional solution diffusion that is coupled with a permeance and selectivity enhancing carrier-mechanism. Therein, the solubility of certain feed component(s) is increased in the membrane through reversible interaction with a carrier agent. Consequently, the interacting component(s) are more readily transferred across the membrane over other non-interacting components. For example, membranes that were useful for separation of alkenes from alkanes incorporated silver ions while other membranes that were useful for separation of carbon dioxide from other gases incorporated amine groups as carrier agents. The silver ions increased the solubility of an alkene over an alkane through a reversible complexation mechanism while amine groups increased carbon dioxide solubility over other gases through a reversible reaction mechanism. Many of these membranes were hydrophilic and required humidification to operate at commercially-attractive performance levels. Membrane humidification likely weakened carrier-membrane interactions such that the carrier can preferably and reversibly interact with certain components in the feed.

A common humidification method that is used with facilitated-transport membranes is to add water vapor to the feed stream prior to entering the feed-side of a pressure vessel containing the membrane such as by passing the feed through a water bubbler or a wet-membrane contactor. For example, see: Kimura et al. "Facilitated separation of a select gas through an ion exchange membrane," U.S. Pat. No. 4,318,714; Eriksen et al. "Use of silver-exchanged ionomer membranes for gas separation," U.S. Pat. No. 5,191,151; and Feiring, A. E. et al. "Membrane separation of olefin and paraffin mixtures," U.S. Pat. No. 10,029,248. Alternatively, facilitated liquid-barrier membrane systems were investigated in which a carrier agent, dissolved in solution comprising liquid water, may be contained within the pores of a support structure or between separate support structures, such as with flat sheet or hollow fiber membranes. Some of the liquid-barrier membranes may be resupplied with additional or excess carrier agent in solution to maintain permeance and selectivity. For examples of liquid barrier membranes see: Sirkar, K. K. "Selective-permeation gas-separation process and apparatus," U.S. Pat. No. 4,750,918; Teramoto et al., "Separation of ethylene from ethane by a flowing liquid membrane using silver nitrate as a carrier," *Journal of Membrane Science* 1989 45 (1-2) 115-136; and Valus, R. J. et al., "High pressure facilitated membranes for selective separation and process for the use thereof," U.S. Pat. No. 5,057,641.

The performance of non-porous facilitated-transport membranes with humidified feed-gas streams was known to be proportional to water-vapor pressure or humidity level, and membranes operated at higher relative humidity had higher permeance and selectivity. However, water-vapor pressure in the feed is limited by the system temperature and corresponding water-saturation (dew) point. At high feed pressures, which are desirable for economical operation, the equilibrium water-content in the membrane was reduced as a result of a lower water mole-fraction in the feed and a higher permeate flux. This resulted in lower permeance (pressure normalized flux) and selectivity as feed-pressure increased. Furthermore, engineering controls to prevent liquid water condensation on the membrane feed-surface at near-saturation pressures become increasingly challenging and costly at high feed-pressure operating conditions.

SUMMARY OF THE INVENTION

This invention discloses a method for humidification of a facilitated-transport membrane in which a non-selective hydration fluid comprising liquid water is brought within the permeate side of a pressure vessel that contains the facilitated-transport membrane (permeate-side humidification). This is unlike known humidification of a permeate-gas sweep in which a gas or gas composition that is different than the permeate gas is separately humidified and subsequently passed through the permeate side of the pressure vessel. Herein, the non-selective hydration fluid comprising liquid water and the permeate-side interface of the facilitated-transport membrane are in communication within the pressure vessel. Communication means that liquid water or water vapor from the non-selective hydration fluid is contacting the permeate-side interface of the facilitated-transport membrane. The facilitated-transport membrane may be in the form of a flat sheet, hollow fiber, or spiral-wound membrane module. The facilitated-transport membrane is preferably non-porous and may also comprise other layers such as a high-diffusion rate (gutter) layer and a porous support in a composite membrane construction.

The non-selective hydration fluid comprising liquid water is non-selective in that it does not contain a carrier agent.

That is, there are no compounds dissolved in the non-selective hydration fluid that would increase the solubility of any of the components in the permeate gas stream through reversible reaction or complexation mechanisms. An exemplary non-selective hydration fluid may consist essentially of liquid water, and may be purified liquid-water being 99% or more liquid water, or 99.5% liquid water or may consist of liquid water. In another embodiment, the non-selective hydration fluid may contain other components such as surfactants, which may enhance the humidification of the facilitated-transport membrane, or other soluble compounds such as corrosion inhibitors. Water as either a liquid or vapor from the non-selective hydration fluid diffuses through the permeate-side interface to humidify the facilitated-transport membrane and increase permeance and selectivity performance. The non-selective hydration fluid may be used herein at temperatures that are between its freezing and boiling points. Preferably, temperatures are between 5 and 60 Celsius and are more preferably between 40 and 60 Celsius. Humidification is more efficient at higher temperatures with correspondingly higher water-vapor pressures where much of the water vapor remains in the smaller permeate flow.

Permeate-side humidification at high operating feed-pressures can be less complex than traditional feed-gas humidification. That is, requirements for precise temperature control between a separate humidification unit-operation of a large feed-gas flow and the membrane may be minimized with use of the non-selective hydration-fluid comprising liquid water within the permeate-side of the pressure vessel. The non-selective hydration fluid may also be at an equivalent or slightly lower pressure than the permeate gas and may also function as a permeate sweep to reduce the permeate concentration at the permeate-side interface and enhance overall membrane selectivity. The permeate gases form bubbles within the non-selective hydration fluid that either move away from the permeate-side interface due to buoyancy or are swept away in a flowing or recirculating non-selective hydration-fluid system. The non-selective hydration fluid may be replenished as it diffuses into the membrane, evaporates, or moves away from the membrane with the permeate bubbles.

Certain exemplary embodiments of the present invention are described herein. The described embodiments are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention. Certain additional terms are also used and some of them are further defined within the following detailed description of the invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. In addition, use of "a" or "an" are employed to describe elements and components described herein. This is done merely for convenience and to give a general sense of the scope of the invention. This description should be read to include one or at least one and the singular also includes the plural unless it is obvious that it is meant otherwise.

BRIEF DESCRIPTION OF SEVERAL VIEWS OF THE DRAWINGS

The accompanying figures are included to provide a further understanding of the invention and are incorporated in and constitute a part of this specification. The figures illustrate embodiments of the invention and together with the description serve to explain the principles of the invention. Corresponding reference characters indicate corresponding parts throughout the views of the figures. The figures represent an illustration of some of the embodiments of the present invention and are not to be construed as limiting the scope of the invention in any manner. Furthermore, the figures are not necessarily to scale and some features may be exaggerated to show details of particular components. Also, specific structural and functional details disclosed herein are not to be interpreted as limiting, but merely as a representative basis for teaching one skilled in the art to variously employ the present invention.

DETAILED DESCRIPTION OF THE INVENTION

Figure 1:
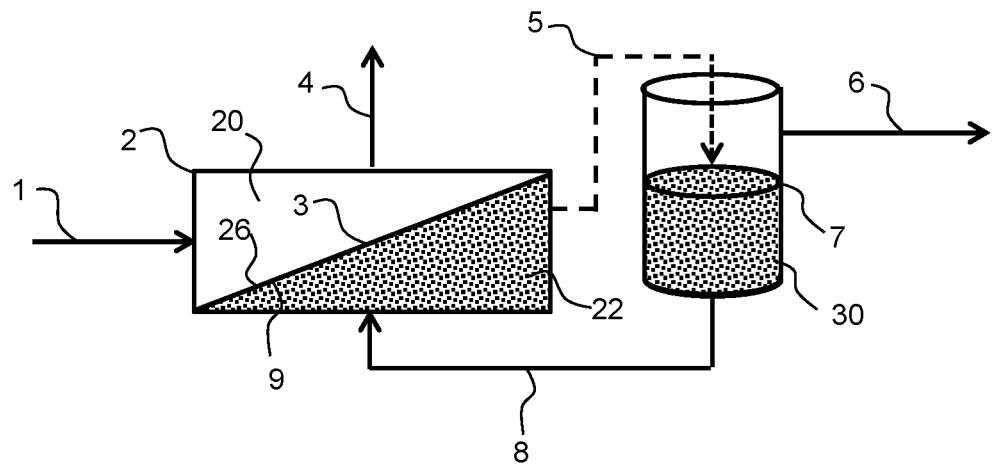
FIG. 1 shows a diagram of an exemplary gas separation system incorporating permeate side humidification via gravity feed of a non-selective hydration fluid to a pressure vessel separated by a facilitated-transport membrane into a feed side and a permeate side.
Figure 2:
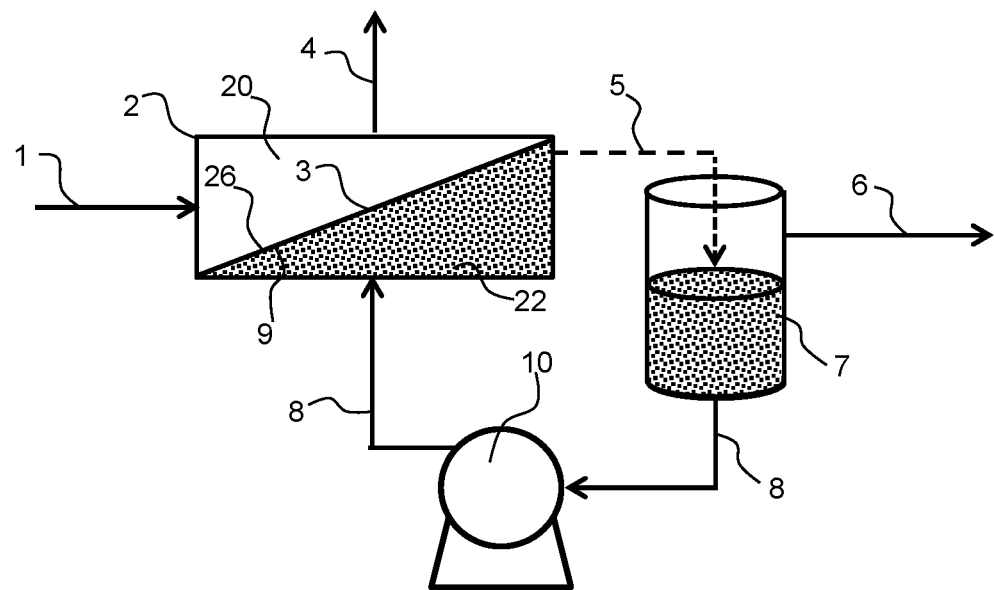
FIG. 2 shows a diagram of an exemplary gas separation system incorporating permeate side humidification via a non-selective hydration fluid that is pumped to the permeate side of a pressure vessel separated by a facilitated-transport membrane into a feed side and a permeate side.

FIGS. 1 and 2 depict two general embodiments for permeate-side humidification of a facilitated-transport membrane that may be in the form of a flat sheet, hollow fiber, or spiral-wound membrane module. Therein, a non-selective hydration fluid 30 comprising liquid water is fed by gravity or circulated using a pump to the permeate side of the pressure vessel 2 that contains the facilitated transport membrane 3. The non-selective hydration fluid is in communication with the permeate-side interface 9 of the facilitated-transport membrane 3. With communication, water vapor or liquid water from the non-selective hydration fluid in the pressure vessel 2 contacts the permeate-side interface 9 of the facilitated-transport membrane 3. Permeate gas may move away from the permeate-side interface 9 and the permeate side of the pressure vessel 2 as bubbles due to buoyancy and within the flow of the non-selective hydration fluid that is circulating into permeate conduit 5. The two phase flow enters reservoir/decanter 7 where the permeate gas and non-selective hydration fluid separate. The permeate gas then exit reservoir/decanter 7 through conduit 6.

As shown in FIG. 1, a facilitated-transport membrane 3 is humidified with a non-selective hydration fluid 30 comprising liquid water that is circulated by gravity. The generic pressure vessel 2 is separated by the facilitated-transport membrane 3 into a feed side 20 and a permeate side 22. A facilitated-transport membrane may be in the form of a flat sheet, hollow fiber, or spiral-wound module and has a feed-side interface 26 exposed to the feed side 20 of the pressure vessel 2 and a permeate-side interface 9 on the permeate side 22 of the pressure vessel. The pressure vessel has a feed inlet 1 and a retentate outlet 4. The non-selective hydration fluid is stored in reservoir/decanter 7 and is gravity fed to the permeate side 22 of the pressure vessel through conduit 8 and may be in contact with the permeate-side interface 9 of the facilitated-transport membrane 3 as a liquid. Permeate gas bubbles may move away from the permeate-side interface 9 through buoyancy and into the permeate conduit 5. The permeate gases and any non-selective hydration fluid that is entrained in the flow enter reservoir/decanter 7 where they separate. The permeate gases exit reservoir/decanter 7 through conduit 6. The reservoir/decanter 7 position is important and should be at a similar height or higher than the generic vessel 2 for the no-selective hydration fluid system to function.

As shown in FIG. 2, a facilitated-transport membrane 3 is humidified with a non-selective hydration fluid 30 comprising liquid water that is circulated by a pump 10. The generic pressure vessel 2 is separated by the facilitated-transport membrane 3 into a feed side 20 and a permeate side 22. The generic pressure vessel 2 having a feed inlet 1 and a retentate outlet 4, contains a facilitated-transport membrane 3 that can be in the form of a flat sheet, hollow fiber, or spiral-wound module. The facilitated-transport membrane has a feed-side interface 26 and permeate-side interface 9. The non-selective hydration fluid is stored in reservoir/decanter 7 and is fed to the permeate-side interface 9 of the facilitated-transport membrane 3 through conduit 8 using pump 10. Permeate gas bubbles may move away from the permeate-side interface 9 through buoyancy or with the flowing non-selective hydration fluid into permeate conduit 5. The two phase flow comprising permeate gases and non-selective hydration fluid enter reservoir/decanter 7 where they separate. The permeate gases exit reservoir/decanter 7 through conduit 6. The reservoir/decanter 7 position relative to membrane separation unit 2 may not be critical with use of pump 10.

Figure 3:
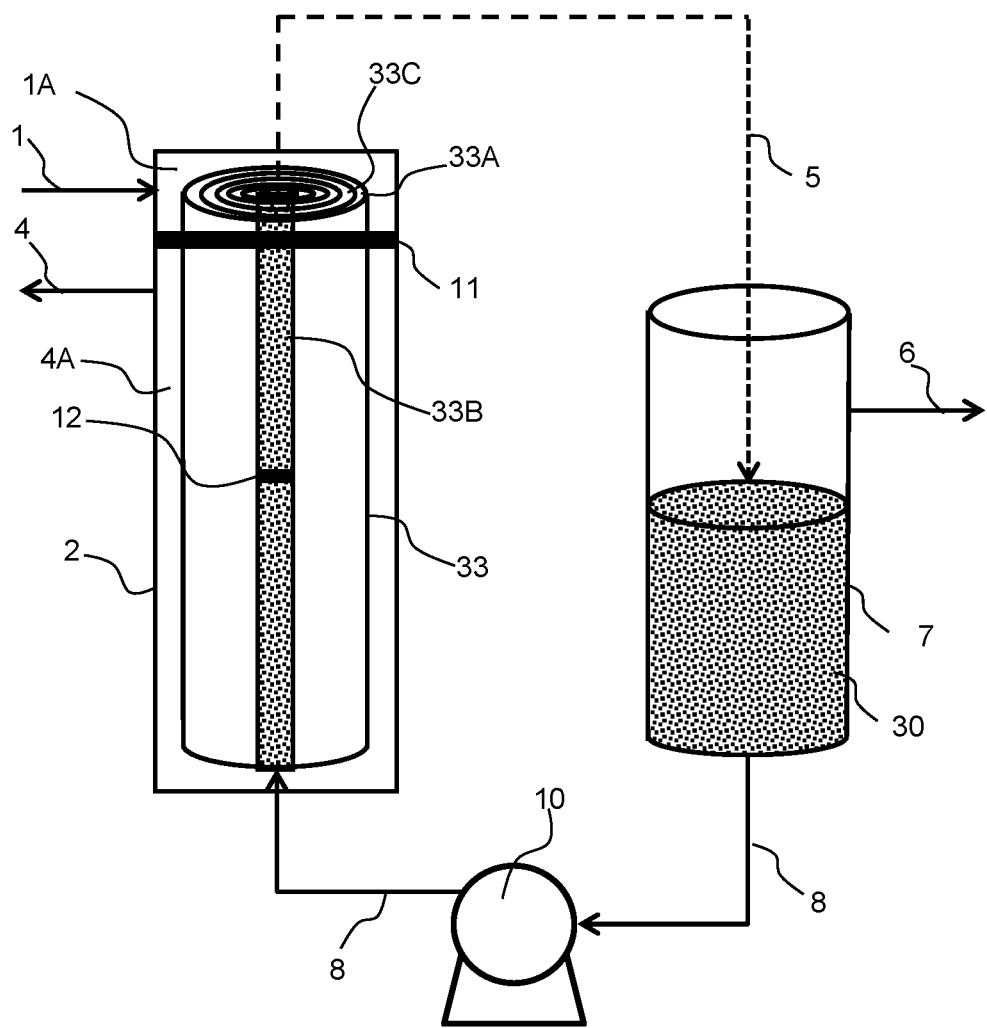
FIG. 3 shows a diagram of an exemplary module gas separation system incorporating permeate side humidification via non-selective hydration fluid that is pumped into the pressure vessel containing the module.

As shown in FIG. 3, an exemplary module gas separation system incorporates permeate side humidification via non-selective hydration fluid 30 that is pumped by pump 10 into the pressure vessel 2 containing a spiral-wound membrane module 33. The non-selective hydration fluid is stored in reservoir/decanter 7 and is fed through conduit 8 using pump 10 to the core tube 33B of a spiral-wound membrane module 33. The core tube 33B has an optional core-tube divider 12 to divert hydration fluid through the membrane leaves 33A. The spiral-wound membrane module 33 is contained within a pressure vessel 2 having a divider 11, which separates the feed chamber 1A from the retentate chamber 4A. Feed gases enter the feed chamber 1A through feed inlet 1 and enter the spiral-wound membrane module 33 through feed-channel spacers 33C that are coaxially wound between the membrane leaves 33A. Feed gases flow parallel to the long axis of the module 33 and exit into retentate chamber 4A, where they exit through retentate outlet 4. Permeate gas or bubbles flow perpendicularly to the feed-gas direction and spirally within the membrane leaves 33A where they converge in the core tube 33B. The two phase flow comprising permeate gases and non-selective hydration fluid in conduit 5 enter reservoir/decanter 7 where they separate. The permeate gases exit reservoir/decanter 7 through conduit 6. The reservoir/decanter 7 position relative to the spiral-wound membrane module 33 may not be critical when used with pump 10.

For large scale commercial applications, spiral-wound membrane modules are highly useful and are an efficient means to assemble flat-sheet membranes having large areas into a compact volume. Spiral-wound membrane modules may also be used in the invention and their design and construction are well documented in the literature. For example see: Scott, K., "Spiral Wound Modules," *Handbook of Industrial Membranes* 1995 pp. 3-185, https://doi.org/10.1016/B978-185617233-2/50004-0; and Johnson, J. E., "Design and Construction of Commercial Spiral Wound Modules," Encyclopedia of Membrane Science and Technology 2013 https://doi.org/10.1002/9781118522318.emst071, which are hereby incorporated in their entirety by reference. Therein as generally described, flat-sheet membranes are formed into a sandwich or membrane leaf with porous-mesh spacers for feed and permeate gas flows. These are wrapped around a core tube and permeate gas flow is collected in the core tube by means of channels or holes in the core tube that are connected to the permeate spacers. Other spiral-wound module designs may be constructed in a similar manner that will allow for a sweep gas or fluid to circulate through the permeate side of the membrane leaf in addition to the core tube. This can be achieved by adding flow-directing elements to the core tube and within the permeate spacers of the membrane leaf. Spiral-wound membrane modules that incorporate multiple membrane leaves for even larger areas and reduced back pressure may also be used in the invention.

FIG. 3 depicts a detailed embodiment for a permeate-side humidification process of a spiral-wound membrane module 3 that contains a facilitated-transport membrane. The non-selective hydration fluid comprising liquid water is stored in reservoir/decanter 7 and is fed through conduit 8 using a pump 10 to the core tube 3b of the spiral-wound membrane module 3. The core tube 3b may contain an optional directing element 12 for circulation of the non-selective hydration fluid across the permeate-side interface of the membrane leaves 3a. Herein, circulation through the core tube 3b alone resulted in good gas separation efficiency in most cases. In this configuration, the non-selective hydration fluid was in communication with the permeate-side interface of the membrane leaves 3a through contact with water vapor that had evaporated from the non-selective hydration fluid and permeated through the holes in the core tube 3b. Permeate gas as bubbles enter the core tube 3b and the two-phase flow with the non-selective hydration fluid moves through conduit 5 and enter into reservoir/decanter 7 where they separate. The permeate gas exits reservoir/decanter 7 through conduit 6.

The invention may be used for a wide variety of gas separations using facilitated-transport membranes that are non-porous and where humidification is desirable or required for gas-separation efficiency. For example, these can include membranes for separation of carbon dioxide from other gases such as disclosed in: Huang, J. et al., "Carbon Dioxide Capture Using a $CO_2$-Selective Facilitated Transport Membrane," Ind. Eng. Chem. Res. 2008 47 1261-1267; Mondal, J. et al., "Synthesis and characterization of crosslinked poly(vinyl alcohol)/poly(allylamine)/2-amino-2-hydrohydroxymethyl-1,3-prapanediol/polysulfone composite membrane for $CO_2/N_2$ separation," *Journal of Membrane Science* 2013 446 383-394; and Tong, Z. et al., "New sterically hindered polyvinylamine membranes for $CO_2$ separation and capture," *Journal of Membrane Science* 2017 543 202-211, which are hereby incorporated in their entirety by reference. Facilitated-transport membranes that are fabricated from polymer materials that are ionomers are also highly useful in the invention. The ionomer-based membranes may be used for separation of alkenes from alkanes, alkenes from non-hydrocarbon gases, in addition to separation of carbon dioxide from other gases.

An ionomer is a copolymer that comprises both electrically neutral repeating units and repeat units having ionic groups. Ionic groups include for example sulfonic acid, sulfonate, sulfonamides, carboxylic acid, carboxylate, phosphate, phosphonium, and ammonium. Ionomers containing pendant sulfonate groups are noted for their applications in facilitated-transport membranes for separation of alkenes from alkanes such as those disclosed in Eriksen et al., "Use of silver-exchanged ionomer membranes for gas separation," U.S. Pat. No. 5,191,151; Feiring, A. E. et al., "Membrane separation of olefin and paraffin mixtures," U.S. Pat. No. 10,029,248; and Wu, M. L., "Gas separations using membranes comprising perfluorinated polymers with pendant ionomeric moieties," U.S. Pat. No. 4,666,468, which are hereby incorporated in their entirety by reference. The ionomer equivalent weight is the weight of ionomer containing one mole of ionic groups. A preferred ionomer equivalent weight for a facilitated-transport membrane useful in the invention is less than 5000 grams per mole, more preferably less than 2000, and very preferably between 500 and 1000-g/mole. The ionomers are preferably fluoropolymers (fluorinated ionomers) that may be known for their high chemical and thermal stability. More preferably, the fluorinated ionomers contain 50% or more carbon-fluorine groups to carbon-hydrogen groups. Very preferred ionomers are fluoropolymers in which there are no carbon-hydrogen groups in the polymer-backbone repeating units. Examples of the latter ionomers are well known in the art and include copolymers comprising repeat units from tetrafluoroethylene and a perfluorovinylether, having a pendant sulfonate group, such as for example Aquivion® (Solvay, Houston, TX) or Nafion® (Chemours, Wilmington, DE).

The facilitated-transport membranes contain a carrier agent. Carrier agents are species that increase the solubility of certain components in the feed gas stream through reversible reaction or complexation mechanisms and preferably "facilitate" their transport across the membrane. The carrier agents may be covalently or electrostatically bound within the membrane to prevent their loss in situations of direct contact with the non-selective hydration fluid comprising liquid water. For example, group 11 metal ions such as silver may be electrostatically bound within facilitated-transport membranes that based on ionomers for use in separations of alkenes from alkanes. Furthermore, amines are known carrier agents for carbon dioxide separations. For example, amine functionally may be covalently bound within a membrane or electrostatically bound within a fluorinated ionomer membrane using certain amines such as polyamines through partial reaction with an ionomer acid-group to form ammonium or alkyl-ammonium cations.

The facilitated transport membranes may be used in the invention in forms such as tubes and flat sheets and they may be monolithic but are preferably thin and part of a composite construction that comprises other layers. These other layers may include a high-diffusion rate (gutter) layer for better permeance, a porous support for thin-layer stability, and a non-woven porous backing for high overall durability for fabrication into more complex geometries such as a spiral-wound membrane module, and strength during use. The other layers may also serve to isolate the facilitated-transport membrane from direct contact with liquid water where excessive swelling or dissolution might be detrimental to performance.

EXAMPLES

Example 1

Comparative effect of water vapor in the feed and permeate sweep for propylene separation from propane: A facilitated-transport membrane in a composite membrane construction was fabricated as generally described in Eriksen et al., "Use of silver-exchanged ionomer membranes for gas separation," U.S. Pat. No. 5,191,151; and Feiring, A. E. et al., "Membrane separation of olefin and paraffin mixtures," U.S. Pat. No. 10,029,248. The composite membrane comprised a layer of a silver salt of a fluorinated ionomer on a porous polyvinylidine fluoride (PVDF) support. The composite membrane as a 47 mm diameter (13.9-cm$^2$) coupon was assembled in a stainless-steel cross-flow cell having ports for feed, retentate, sweep, and permeate flows. The feed gas consisted of a mixture of 20-mol % propylene ($C_3H_6$) and 80-mol % propane ($C_3H_8$) at 60-psig and 0.2-SLPM. All or a fraction (half) of the feed flow was humidified using a water bubbler (and recombined) prior to entering the cell. A nitrogen sweep (300-mL/min) was humidified in a similar manner and sweep and permeate flows (<1-psig) were measured using a bubble-flow meter. The membrane was tested at ambient (20 to 25° C.) temperatures and the permeate composition was measured by gas chromatography. Table 1 showed the varied effect of humidity (RH) in the feed and sweep flows on propylene gas permeance units (GPU) and selectivity (α) over propane. The highest propylene permeance and selectivity was demonstrated at 100% RH in both the feed and sweep. The overall performance with 100% RH in the sweep only was higher than with 100% RH in the feed only.

TABLE 1

| | | Sweep | | | | | | | |
|---|---|---|---|---|---|---|---|---|---|
| | | 100% Rh | | | 50% Rh | | | 0% Rh | | |
| | | Permeance GPU | | | Permeance GPU | | | Permeance GPU | | |
| | | C3H8 | C3H6 | α | C3H8 | C3H6 | α | C3H8 | C3H6 | α |
| Feed | 100% Rh | 1.93 | 200.13 | 103.8 | 1.55 | 73.98 | 47.9 | 1.71 | 20.20 | 11.8 |
| | 50% Rh | 2.04 | 171.99 | 84.2 | 2.04 | 29.11 | 14.3 | 1.95 | 6.09 | 3.1 |
| | 0% Rh | 2.26 | 67.46 | 29.9 | 2.16 | 9.92 | 4.6 | 1.99 | 3.18 | 1.6 |

Example 2

Humidification method and pressure effect on membrane ethylene permeance and selectivity over ethane: A facilitated-transport membrane was fabricated as described in example 1 and a 47-mm diameter coupon (13.9-cm$^2$) from the membrane was placed in the stainless-steel test cell. The test cell was configured as outlined in FIG. 1 for testing with and without addition of a non-selective hydration fluid consisting of de-ionized water to the permeate-side of the test cell through the sweep port. The feed gas consisted of a mixture of 20-mol % ethylene and 80-mol % ethane at 0.2-SLPM and 60 or 200-psig. The feed-gas flow was optionally humidified using a water bubbler prior to entering the cell. The membrane was tested at ambient (20 to 25° C.) temperatures. Permeate flows (<1-psig) were measured using a bubble-flow meter and composition was measured by gas chromatography. Table 2 showed that ethylene permeance at high feed pressures was notably higher with the addition of de-ionized water to the permeate side of the test cell.

TABLE 2

| Humidification Conditions | | Feed Pressure | Ethylene Permeance | Ethylene/ Ethane |
|---|---|---|---|---|
| Feed | Permeate | (psig) | (GPU) | Selectivity |
| Humidified | Dry | 60 | 246 | 34.9 |
| Humidified | Wet | 60 | 203 | 28.2 |
| Dry | Dry | 200 | 4.0 | 3.0 |
| Humidified | Dry | 200 | 52.3 | 10.1 |
| Dry | Wet | 200 | 114 | 56.4 |
| Humidified | Wet | 200 | 111 | 51.4 |

Example 3

Humidification method and pressure effect on propylene permeance and selectivity over propane for a spiral-wound membrane module: Two facilitated-transport membranes (A and B) were fabricated as described in example 1 and separately assembled into spiral-wound membrane modules as described by reference in the specification. The membrane active areas were approximately 1.7-ft$^2$ (1600-cm$^2$). Separately, the spiral-wound membrane modules were assembled and orientated vertically in a stainless-steel pressure vessel as outlined in FIG. 3 and tested as outlined in FIG. 1 with and without de-ionized water addition by gravity to the core tube of the module. The feed gas consisted of a mixture of 20-mol % propylene and 80-mol % propane at 0.2-SLPM and 60 or 90-psig. The feed-gas flow was optionally humidified using a water bubbler prior to entering the pressure vessel. The modules were tested at ambient (20 to 25° C.) temperatures, permeate flows (<1-psig) were measured using a bubble-flow meter, and composition was measured by gas chromatography. Table 3 showed that propylene permeance at the higher 90-psig feed pressure had significantly increased with the addition of de-ionized water to the core tube for both of the spiral-wound membrane modules.

TABLE 3

| Membrane | Humidification Conditions | | Feed Pressure | Propylene Permeance | Propylene/ propane |
|---|---|---|---|---|---|
| | Feed | Permeate | (psig) | (GPU) | Selectivity |
| A | Dry | Dry | 60 | 3.9 | 3.5 |
| A | Humidified | Dry | 60 | 102 | 27 |
| A | Dry | Wet | 60 | 100 | 14.4 |
| A | Humidified | Dry | 90 | 28.0 | 30.3 |
| A | Humidified | Wet | 90 | 119 | 29.0 |

TABLE 3-continued

| Membrane | Humidification Conditions | | Feed Pressure | Propylene Permeance | Propylene/ propane |
|---|---|---|---|---|---|
| | Feed | Permeate | (psig) | (GPU) | Selectivity |
| B | Humidified | Dry | 90 | 21.3 | 11.8 |
| B | Humidified | Wet | 90 | 155 | 23.5 |

Example 4

Propylene permeance and selectivity over propane for a spiral-wound membrane module with continuous recirculation of water through the core tube: A facilitated-transport membrane was fabricated as described in example 1 and assembled into spiral-wound membrane modules as described by reference in the specification. The membrane active area was approximately 1.7-ft$^2$ (1600-cm$^2$). The spiral-wound membrane modules were assembled and orientated vertically in a stainless-steel pressure vessel as outlined in FIG. 3 and tested with and without de-ionized water addition and recirculation using a pump to the core tube of the module. The feed gas consisted of a mixture of 20-mol % propylene and 80-mol % propane at 0.2-SLPM and 90-psig. The feed-gas flow was not humidified prior to entering the pressure vessel. The module ware tested at ambient (20 to 25° C.) temperature, permeate flows (<1-psig) were measured using a bubble-flow meter, and permeate compositions were measured by gas chromatography. Table 4 showed a high steady-state propylene permeance and selectivity over propane with humidification of the membrane permeate-side through recirculation of de-ionized water through the core tube only.

TABLE 4

| Humidification Conditions | | Propylene Permeance | Propylene/ propane |
|---|---|---|---|
| Feed | Permeate | (GPU) | Selectivity |
| Dry | Dry | 1.9 | 5.2 |
| Dry | Wet | 92.7 | 32.7 |

What is claimed is:

1. A process for separating a gaseous mixture using a facilitated-transport membrane, the process comprising:
   a) delivering a non-selective hydration fluid comprising liquid water to a permeate side of a pressure vessel containing the facilitated-transport membrane;
   b) exposing a feed interface side of the facilitated-transport membrane to a flowing gaseous first mixture consisting of at least two components; and
   c) producing a second gaseous mixture that is enriched in at least one of the components of the first mixture on a permeate side of the facilitated-transport membrane,
   wherein the facilitated-transport membrane comprises an ionomer and is a component of a composite construction comprising a layer that isolates the facilitated-transport membrane from contact with the liquid water, thereby avoiding excessive swelling or dissolution of the facilitated-transport membrane due to the contact with the liquid water.

2. The process of claim 1, wherein the facilitated-transport membrane comprises a fluorinated ionomer.

3. The process of claim 2, wherein the fluorinated ionomer comprises 50% or more carbon-fluorine groups to carbon-hydrogen groups.

4. The process of claim 1, wherein the facilitated-transport membrane comprises a carrier agent selected from a group consisting of silver ions, ammonium ions, alkyl-ammonium ions, an amine and a polyamine.

5. The process of claim 1, wherein the non-selective hydration fluid is delivered to a core tube of a spiral-wound membrane module that incorporates the facilitated-transport membrane, said core tube being situated within the permeate side of the pressure vessel.

6. The process of claim 1, wherein the non-selective hydration fluid is static within the pressure vessel.

7. The process of claim 1, wherein the flowing gaseous first mixture comprises an alkene.

8. The process of claim 1, wherein the flowing gaseous first mixture comprises carbon dioxide.

9. The process of claim 1, wherein the flowing gaseous first mixture comprises at least one selected from the group consisting of an alkane, nitrogen, hydrogen, and water vapor.

10. The process of claim 1, wherein the non-selective hydration fluid is flowing within the pressure vessel.

11. The process of claim 1, wherein the non-selective hydration fluid is in contact with a permeate interface side of the facilitated-transport membrane.

12. The process of claim 1, wherein the non-selective hydration fluid consists essentially of water, such that the liquid water constitutes at least 99% of the non-selective hydration fluid.

13. The process of claim 1, wherein the non-selective hydration fluid comprises a surfactant.

14. The process of claim 1, wherein the non-selective hydration fluid comprises a corrosion inhibitor.

\* \* \* \* \*